United States Patent
Sos et al.

(10) Patent No.: US 10,179,225 B2
(45) Date of Patent: Jan. 15, 2019

(54) ATRAUMATIC MICROPUNCTURE GUIDEWIRE AND GUIDEWIRE EXTENSION

(71) Applicants: Thomas A. Sos, New York, NY (US); Mitchell Tatum, Austin, TX (US)

(72) Inventors: Thomas A. Sos, New York, NY (US); Mitchell Tatum, Austin, TX (US)

( * ) Notice: Subject to any disclaimer, the term of this patent is extended or adjusted under 35 U.S.C. 154(b) by 0 days.

(21) Appl. No.: 15/055,282

(22) Filed: Feb. 26, 2016

(65) Prior Publication Data

US 2016/0250447 A1     Sep. 1, 2016

Related U.S. Application Data

(60) Provisional application No. 62/192,392, filed on Jul. 14, 2015, provisional application No. 62/137,583, filed on Mar. 24, 2015, provisional application No. 62/136,733, filed on Mar. 23, 2015, provisional application No. 62/121,589, filed on Feb. 27, 2015.

(51) Int. Cl.
*A61M 25/09* (2006.01)
*A61M 25/01* (2006.01)

(52) U.S. Cl.
CPC .... *A61M 25/0905* (2013.01); *A61M 25/0133* (2013.01); *A61M 25/09041* (2013.01); *A61M 2025/0163* (2013.01); *A61M 2025/09083* (2013.01); *A61M 2025/09133* (2013.01); *A61M 2025/09175* (2013.01); *A61M 2205/0266* (2013.01)

(58) Field of Classification Search
CPC ............ A61M 25/09; A61M 25/09025; A61M 2025/09058; A61M 2025/0915; A61M 2025/09175

USPC ........................................ 600/433, 434, 585
See application file for complete search history.

(56) References Cited

U.S. PATENT DOCUMENTS

| | | |
|---|---|---|
| 4,796,642 A | 1/1989 | Harris |
| 4,846,186 A | 7/1989 | Box et al. |
| 4,935,008 A | 6/1990 | Lewis, Jr. |

(Continued)

OTHER PUBLICATIONS

International search report and written opinion dated Jul. 14, 2016 for PCT/US2016/019746.

(Continued)

*Primary Examiner* — Jeffrey G Hoekstra
*Assistant Examiner* — Jonathan M Foreman
(74) *Attorney, Agent, or Firm* — Wilson Sonsini Goodrich & Rosati

(57) ABSTRACT

A guidewire introducable into a bodily lumen having an obstruction therein is provided. An introducer needle is advanced through tissue and into the bodily lumen. A guidewire is advanced through the introducer and into the lumen. The guidewire is advanced further through the lumen until an atraumatic distal tip of the guidewire encounters an obstruction the distal tip cannot pass in a straight forward manner. The distal tip is pressed against the obstruction such that a flexible segment proximal of the distal tip forms a loop distal of the distal tip. The guidewire is advanced further through the lumen such that the loop of the flexible segment is pushed past the obstruction and the distal tip is pulled distally past the obstruction. A greater diameter guidewire extension can be coupled to the back end of the guidewire, providing function as a larger diameter guidewire.

27 Claims, 16 Drawing Sheets

(56) References Cited

U.S. PATENT DOCUMENTS

| | | | |
|---|---|---|---|
| 4,991,602 A | 2/1991 | Amplatz et al. | |
| 5,060,660 A | 10/1991 | Gambale et al. | |
| 5,109,867 A | 5/1992 | Twyford, Jr. | |
| 5,133,364 A | 7/1992 | Palermo et al. | |
| 5,282,478 A | 2/1994 | Fleischhaker, Jr. et al. | |
| 5,368,049 A | 11/1994 | Raman et al. | |
| 5,507,729 A * | 4/1996 | Lindenberg | A61M 25/09 600/585 |
| 5,513,650 A | 5/1996 | Johansen | |
| 5,725,534 A * | 3/1998 | Rasmussen | A61M 25/09 600/585 |
| 5,836,892 A * | 11/1998 | Lorenzo | A61M 25/09 600/433 |
| 6,113,579 A | 9/2000 | Eidenschink et al. | |
| 6,139,510 A * | 10/2000 | Palermo | A61L 31/022 600/585 |
| 6,524,301 B1 | 2/2003 | Wilson et al. | |
| 7,169,118 B2 | 1/2007 | Reynolds et al. | |
| 7,824,345 B2 | 11/2010 | Euteneuer et al. | |
| 7,883,474 B1 * | 2/2011 | Mirigian | A61M 25/09 600/585 |
| 2004/0199088 A1 * | 10/2004 | Bakos | A61M 25/09025 600/585 |
| 2005/0113853 A1 | 5/2005 | Noriega et al. | |
| 2009/0187147 A1 | 7/2009 | Kurth et al. | |
| 2011/0071435 A1 | 3/2011 | Shamay et al. | |
| 2016/0008584 A1 * | 1/2016 | Root | A61M 25/09 604/510 |
| 2017/0021140 A1 | 1/2017 | Sos et al. | |

OTHER PUBLICATIONS

Office action dated Jan. 26, 2017 for U.S. Appl. No. 15/289,056.
Office action dated Jun. 16, 2017 for U.S. Appl. No. 15/289,056.
Office Action dated Sep. 18, 2017 for U.S. Appl. No. 15/289,056.
Notice of Allowance dated Apr. 13, 2018 for U.S. Notice of Allowance U.S. Appl. No. 15/289,056.

* cited by examiner

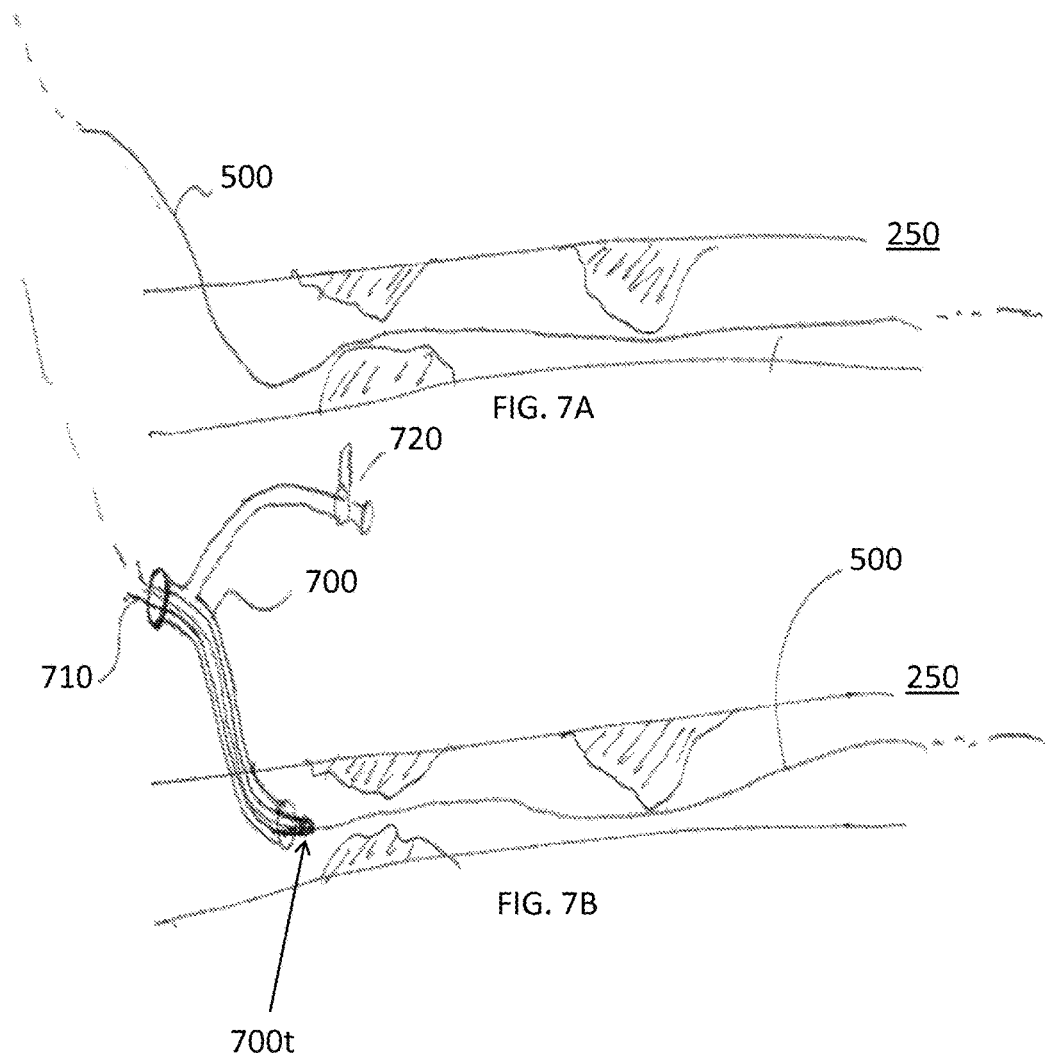

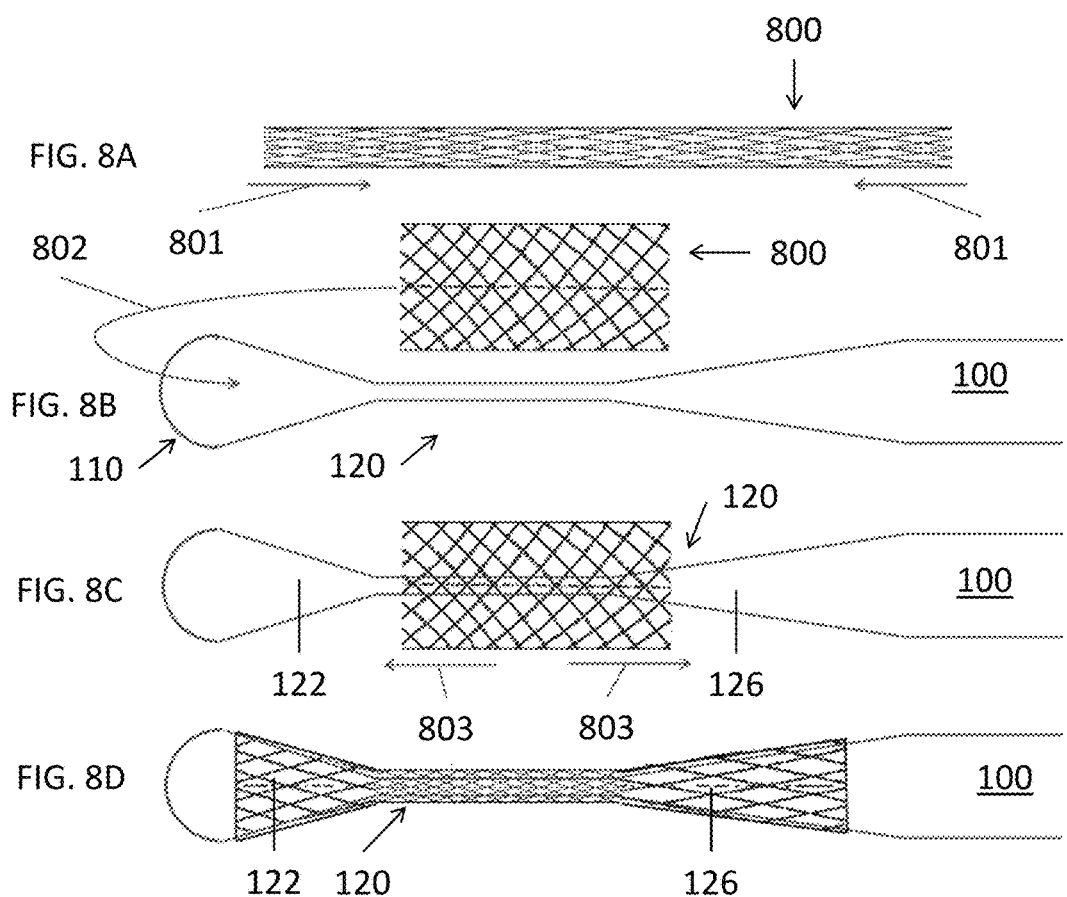

ATRAUMATIC MICROPUNCTURE GUIDEWIRE AND GUIDEWIRE EXTENSION

CROSS-REFERENCE

This application claims the benefit of the following provisional patent applications: Ser. Nos. 62/192,392, filed Jul. 14, 2015, 62/137,583, filed Mar. 24, 2015, 62/136,733, filed Mar. 23, 2015 and 62/121,589, filed Feb. 27, 2015, the contents of which are fully incorporated herein by reference.

BACKGROUND

The present disclosure relates to medical devices, systems, and methods. In particular, the present disclosure relates to guidewires used in micropuncture sets and many medical procedures.

Many minimally invasive medical procedures rely on catheters and other similar devices introduced and advanced through the vasculature or other bodily lumens. In many cases, such devices are advanced over a guidewire that has been navigated through the vasculature or bodily lumen. Often, the guidewire itself has been introduced first through an introducer needle puncturing tissue and accessing the vasculature or other bodily lumen and then through the vasculature or bodily lumen. The guidewire may then be advanced and navigated toward a target region.

In some medical procedures, small diameter or micropuncture guidewires may be used. For example, regular guidewires may have a diameter of about 0.035" while micropuncture guidewires may have a diameter of 0.018". Current micropuncture guidewires may be less than ideal in at least some cases. For example, many micropuncture guidewires may encounter a high degree of friction as they are advanced through the lumen of a small gauge introducer needle. Due to the friction, the operator of the guidewire may lose much tactile feedback. It may therefore be difficult for the operator to discern resistance from the guidewire versus resistance from the micropuncture guidewire encountering plaque or other obstructions in the vasculature or bodily lumen. In some cases, the operator may mistake resistance from plaque or the guidewire abutting the wall of the vessel as resistance from the needle, apply excessive forward force to the guidewire, and inadvertently puncture or dissect the wall of a blood vessel with the guidewire tip. Micropuncture guidewires also may have a smaller diameter than standard guidewires. Therefore, the force exerted by the tip of micropuncture guidewires can be concentrated on a smaller area, which may increase the likelihood of perforating, puncturing, or otherwise causing trauma to tissue. An additional risk of using currently available micropuncture sets may be that after removing the micropuncture needle, in order to enlarge the entry hole into the vessel or body lumen, two coaxial dilators, an inner one with a 0.018" inner diameter and an outer one with a 0.035" inner diameter, are typically introduced over the micropuncture guidewire. The inner dilator may then be removed together with the 0.018" guidewire thus leaving in place a 0.035" inner diameter dilator. The remaining outer dilator can allow the introduction of a larger 0.035" guidewire, which must successfully re-cross the segment of the vessel or body cavity which had been previously crossed with the initially introduced 0.018" guidewire. The attempted re-crossing may pose an additional injury threat and it may be difficult or even impossible to successfully re-cross the vessel or body cavity. There are therefore needs for improved micropuncture guidewires to overcome such disadvantages.

References that may be of interest may include U.S. Pat. Nos. 7,824,345, 7,169,118, 5,507,729, 5,368,049, 5,282,478, 5,133,364, 5,060,660, 4,991,602, and 4,796,642 and U.S. Pub. Nos. 2011/0071435 and 2009/0187147. Many of these references show guidewires and extensions with the same diameter and describe nothing specifying or implying the need for or rationale for different diameter guidewires and extensions. Some of these references also specify that guidewires and their extensions be of the same diameter.

SUMMARY

Aspects of the present disclosure provide a guidewire apparatus advanceable through a bodily lumen or vessel. The guidewire apparatus may comprise a rounded distal tip, a flexible neck segment, and an elongate segment. The rounded distal tip may have a first diameter. The flexible, neck segment may be proximal of the rounded distal tip and may have a second diameter less than the first diameter. The flexible neck segment may be straight, curved, or shapeable. The elongate segment may be proximal of the neck segment and may have a third, fourth, or further diameter(s) greater than the second and/or subsequent diameter(s). When the guidewire apparatus encounters an obstruction as it is advanced through the bodily lumen, it may be steered, directed, and advanced past the obstruction as other similar conventional guidewires can be made to do. However, when the guidewire apparatus is unable to be advanced past the obstruction as described, the flexible neck segment may be configured to assume a loop form as the rounded distal tip encounters the obstruction. The loop may be disposed distally of the rounded distal tip when formed. Further advancement of the guidewire may push the loop past the obstruction so that the rounded distal tip is ultimately pulled past the obstruction.

One or more of the rounded distal tip, the flexible neck segment, or the elongate segment may be covered with a coating. The coating may comprise one or more of a radiopaque coating, a hydrophobic coating, a hydrophillic coating, an anti-thrombogenic coating, a polymeric coating, a silicone coating, or a polytetrafluoroethylene (PTFE) coating, to name a few.

The guidewire apparatus may comprise a single piece extrusion or grind without joints or welds. The guidewire apparatus may be made of a material comprising one or more of platinum, gold, silver, NiTi, steel, steel alloy, stainless steel, stainless steel alloy, titanium, titanium alloy, aluminum, aluminum alloy, tungsten, or tungsten alloy, to name a few.

The guidewire apparatus may comprise a micropuncture guidewire. The first diameter, or the diameter of the rounded distal tip, may be about 0.018 inches and the second diameter, or the diameter of the flexible neck segment, may be about 0.010. In some embodiments, the flexible neck segment may comprise (sub) segments or (sub) sections of several diameters which increase proximally with tapered transition(s). For instance, the second diameter, or the diameter of a distal section of the flexible neck segment may be about 0.002 inches; a third diameter, or a diameter of a middle section of the flexible neck segment, may be about 0.004 inches; and, a fourth diameter, or a diameter of a proximal section of the flexible neck segment, may be about 0.010 inches; and, further optionally, a fifth diameter, or a diameter of the elongate section of the guidewire proximal flexible neck segment, may be about 0.018 inches. These dimensions of the guidewire apparatus are disclosed as an example only and other dimensions are contemplated. The guidewire apparatus will typically be scalable and adaptable for other guidewire sizes, such as "standard" non-micropuncture guidewires of any diameter and length. For example, the guidewire apparatus may be adapted for use with a typical 145 cm or 180 cm long and 0.035 inch diameter guidewire, according to many embodiments.

The bodily lumen the guidewire apparatus may be advanced through may comprise a bodily duct, a bodily track, a bodily orifice, a bodily invagination, a blood vessel, an artery, a vein, a urethra, a ureter, a vagina, a fallopian tube, a rectum, a throat, an ear canal, a nasal tract, a bile duct, a biliary tract, an esophagus, a trachea, a bronchus, or an artificial bodily tract or lumen, to name a few. In many embodiments, the bodily lumen comprises a blood vessel and the obstruction comprises plaque therein.

The rounded distal tip may be biased to return to a position distal of the flexible segment after the loop of the flexible neck segment is advanced past the obstruction and the rounded distal tip is pulled past the obstruction. The flexible neck segment may be biased so that the loop straightens after the loop of the flexible neck segment is advanced past the obstruction and the rounded distal tip is pulled past the obstruction.

The elongate segment proximal of the neck segment may comprise a first portion having the third diameter and a second portion having a fourth diameter different than the third diameter. The fourth diameter may be greater than the third diameter. The first portion of the elongate segment may be axially separate from the second portion of the elongate segment. For example, the greater diameter second portion may be proximal (or closer to the user-operated end) of the lesser diameter second portion.

The guidewire apparatus may further comprise a wire braid or coil disposed over and supporting the flexible, neck segment. The wire braid or coil may be attached to the flexible, neck segment. The wire braid or coil may be at least partially disposed over one or more of a distal tapering region between the rounded distal tip and the flexible, neck segment or a proximal tapering region between the elongate segment and the flexible, neck segment. A combined diameter of the wire braid or coil and the flexible, neck segment will typically be less than the third diameter of the elongate segment Aspects of the present disclosure also provide a guidewire apparatus advanceable through a bodily lumen. The guidewire apparatus may comprise an atraumatic distal tip, a flexible segment, and an elongate segment. The atraumatic distal tip may have a first stiffness. The flexible segment may be proximal of the atraumatic distal tip and may have a second stiffness less than the first stiffness. The elongate segment may be proximal of the flexible segment and may have a third stiffness greater than the second stiffness. The flexible segment may be configured to form into a loop as the guidewire apparatus is advanced through the bodily lumen and the atraumatic distal tip encounters an obstruction. The loop may be disposed distally of the atraumatic distal tip when formed. Further advancement of the guidewire may push the loop past the obstruction so that the atraumatic distal tip is pulled past the obstruction.

One or more of the atraumatic distal tip, the flexible segment, or the elongate segment is covered with a coating or several coatings. For example, the atraumatic distal tip may be coated with a soft coating to minimize trauma caused by contact of the distal tip with tissue. Alternatively or in combination, the atraumatic distal tip may be rounded to minimize such potential trauma. The coating may comprise a radiopaque coating, a hydrophobic coating, a hydrophillic coating, an anti-thrombogenic coating, a polymeric coating, a silicone coating, or a polytetrafluoroethylene (PTFE) coating, to name a few.

One or more of the atraumatic distal tip or the elongate segment may comprise a first material, and the flexible segment may comprise a second material different from and more flexible than the first material.

Alternatively, one or more of the atraumatic distal tip or the elongate segment may comprise a first material, and the flexible segment may comprise the same first material. The flexible segment may be mechanically modified to be more flexible than one or more of the atraumatic distal tip or the elongate segment. For example, the flexible segment may have one or more slots or cuts (e.g., cut into the shape of a coil spring) to provide flexibility. One or more of the atraumatic distal tip, flexible segment, or elongate segment may have the same diameter. For example, each of the atraumatic distal tip, flexible segment, and elongate segment may have the same diameter. Alternatively, the flexible segment may have a smaller diameter than the atraumatic distal tip and the elongate segment. In some embodiments, the flexible segment may comprise a neck segment having an hourglass-like shape (i.e., a shape having tapers toward the middle on both axial ends).

Exemplary materials the guidewire apparatus may be made of include platinum, gold, silver, NiTi, steel, steel alloy, stainless steel, stainless steel alloy, titanium, titanium alloy, aluminum, aluminum alloy, tungsten, and tungsten alloy, to name a few.

The bodily lumen the guidewire apparatus may be advanced through may comprise a bodily duct, a bodily track, a bodily orifice, a bodily invagination, a blood vessel, an artery, a vein, a urethra, a ureter, a vagina, a fallopian tube, a rectum, a throat, an ear canal, a nasal tract, a bile duct, a biliary tract, an esophagus, a trachea, a bronchus, or an artificial bodily tract or lumen, to name a few. In many embodiments, the bodily lumen comprises a blood vessel and the obstruction comprises plaque therein.

The atraumatic distal tip may be biased to return to a position distal of the flexible segment after the loop of the flexible segment is advanced through the obstruction and the atraumatic distal tip is pulled through the obstruction. The flexible segment may be biased so that the loop straightens after the loop of the flexible segment is advanced past the obstruction and the atraumatic tip is pulled past the obstruction.

The guidewire apparatus may further comprise a wire braid or coil disposed over and supporting the flexible segment. The braid or wire coil may be attached to the flexible segment. The wire braid or coil may be at least partially disposed over one or more of a distal transition region between the atraumatic distal tip and the flexible segment or a proximal transition region between the elongate segment and the flexible segment. A combined diameter of the wire braid or wire and the flexible, neck segment is less than a diameter of the elongate segment.

Aspects of the present disclosure may further provide a method of introducing a guidewire into a bodily lumen having an obstruction therein. An introducer needle may be advanced through tissue and into the bodily lumen. A guidewire may be advanced through a lumen of the introducer needle and into the bodily lumen. The guidewire may be advanced further through the bodily lumen until an atraumatic distal tip of the guidewire encounters an obstruction. The guidewire may be advanced or steered past these obstructions with its atraumatic tip leading. On occasion, the atraumatic distal tip may not pass and be pressed against the obstruction such that a flexible segment proximal of the atraumatic distal tip forms a loop distal of the atraumatic distal tip. The guidewire may be advanced further through the bodily lumen such that the loop of the flexible segment is pushed past the obstruction and the atraumatic distal tip is pulled distally past the obstruction by the loop of the flexible segment.

After the loop of the flexible segment is advanced past the obstruction and the atraumatic distal tip is pulled distally past the obstruction, the atraumatic distal tip may resiliently return to a position distal of the flexible segment and the loop of the flexible segment may straighten.

The bodily lumen the guidewire may be advanced through may comprise a bodily duct, a bodily track, a bodily orifice, a bodily invagination, a blood vessel, an artery, a vein, a urethra, a ureter, a vagina, a fallopian tube, a rectum, a throat, an ear canal, a nasal tract, a bile duct, a biliary tract, an esophagus, a trachea, a bronchus, or an artificial bodily tract or lumen, to name a few. In many embodiments, the bodily lumen comprises a blood vessel and the obstruction comprises plaque therein.

To support the flexible segment as it is advanced through the bodily lumen, a wire braid or coil may be coupled to the flexible segment. The wire braid or coil may be disposed over the flexible segment.

Aspects of the present disclosure also provide extension guidewire apparatuses for coupling to guidewires, such as the guidewire extensions described above and herein. A guidewire extension apparatus may comprise a far end portion, a near end portion, and a tapering transition portion therebetween. The far end portion may have a first diameter matching a diameter of a near end of the guidewire. The far end portion may be configured to couple with the near end of the guidewire. For example, the far end portion may be configured to couple with the near end of the guidewire with a male-female connection such as a snap-fit, an interference fit, or a threaded fit. The near end portion may have a second diameter greater than the first diameter. For example, the first diameter and the diameter of the near end of the guidewire may be both 0.018", and second diameter of the near end portion is 0.035". One or more of the far end portion, the near end portion, or the tapered portion is covered with a lubricious coating such as any of the coating described above and herein.

Aspects of the present disclosure also provide methods for introducing a micropuncture guidewire, such as the micropuncture guidewire apparatus described above and herein, and a guidewire extension, such as the guidewire extension apparatus described above and herein, into a bodily lumen, such as any of the bodily lumens described above and herein. A micropuncture needle may be penetrated through tissue to access the bodily lumen. The micropuncture guidewire may be advanced through the micropuncture needle and into the bodily lumen such that a near or proximal end of the micropuncture guidewire remains outside of the tissue. The micropuncture needle may be retracted from the tissue and bodily lumen and removed from the micropuncture guidewire. The near or proximal end of the micropuncture guidewire may be coupled to a far or distal end portion of a guidewire extension such as with a male-female connection, for example, a snap-fit, interference joint, or a threaded fit. The near or proximal end of the micropuncture guidewire and the far or distal end portion of guidewire extension may have the same diameter, such as 0.018", while the far end of the guidewire extension may have a greater diameter, such as 0.035". The coupled micropuncture guidewire and guidewire extension may be advanced through the tissue and bodily lumen such that a greater diameter near end portion and a tapering transition portion of the guidewire extension are within the bodily lumen. The tapering transition portion may be disposed between the greater diameter near end portion and the far end portion of the guidewire extension.

Aspects of the present disclosure also provide a sheath introducer apparatus which may be introduced over the micropuncture guidewire. The inner diameter of the sheath may be of various sizes, for example 3, 4, 5, or 6 Fr. The end of the inner dilator may be tapered to the same diameter as the micropuncture guidewire, such as 0.018". The length of the sheath introducer apparatus may be long enough to insert a catheter or other over-the-wire device over the guidewire to access the bodily lumen or vessel. The inner diameter of the catheter or over-the-wire device may be greater than 0.018", such as 0.035".

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIG. 7A shows a side section view of the micropuncture guidewire of FIG. 1 being introduced into a blood vessel and the introducer needle withdrawn;

FIG. 7B shows a side section view of an outer introducer sheath with an inner dilator being introduced into the blood vessel over the micropuncture guidewire of FIG. 1;

FIG. 8A shows a side view of a wire braid to support the flexible neck segment of a guidewire apparatus, according to many embodiments.

FIG. 8B shows the wire braid of FIG. 8A to be advanced over the flexible neck portion.

FIG. 8C shows the wire braid of FIG. 8A advanced over the flexible neck portion and in a radially expanded, foreshortened configuration.

FIG. 8D shows the wire braid of FIG. 8A advanced over the flexible neck portion and in a radially collapsed configuration.

DETAILED DESCRIPTION

Figure 1:
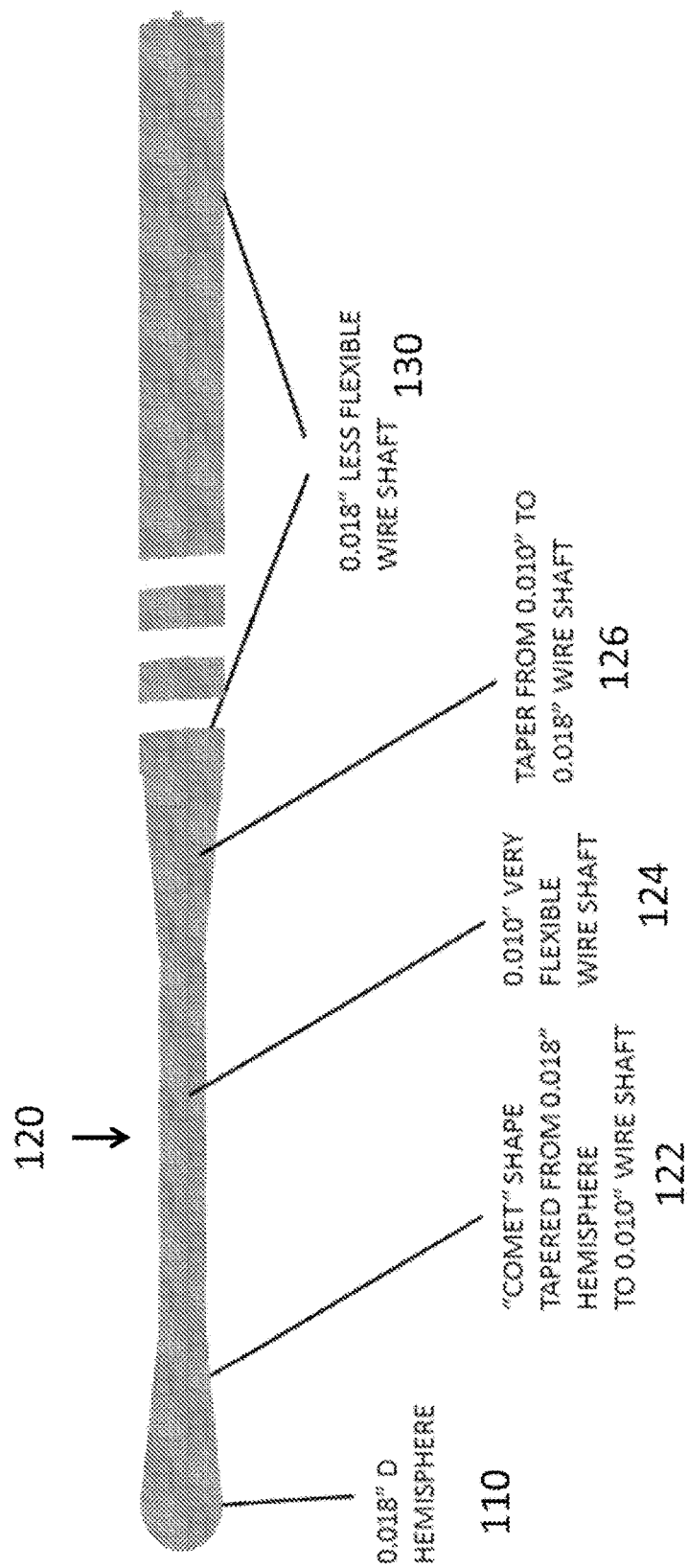
FIG. 1 shows a side view of the distal portion of a micropuncture guidewire, according to many embodiments.

FIG. 1 shows a side view of the micropuncture guidewire 100, according to many embodiments. The micropuncture guidewire 100 may comprise an atraumatic distal tip 110. The atraumatic distal tip 110 may be hemispheric or rounded and/or coated as described herein to minimize trauma to tissue the tip 110 may encounter as the guidewire 100 is advanced or retracted through a bodily lumen. As shown in FIG. 1, the atraumatic distal tip 110 may have a diameter of 0.018". Alternatively, the atraumatic distal tip 110 may have the diameter of a standard guidewire, such as 0.035".

The micropuncture guidewire 100 may further comprise a flexible segment 120 proximal of the atraumatic distal tip 110. The flexible segment 120 may be more flexible than the atraumatic distal tip 110. As shown in FIG. 1, the flexible segment 120 may comprise a distal tapering portion 122, which tapers in the proximal direction. The flexible segment 120 may further comprise a middle, flexible wire shaft portion 124, and a proximal tapering portion 126, which tapers in the distal direction. The diameter of the guidewire 100 at the middle, flexible wire shaft portion 124 may be 0.010" or 0.0070", for example. Alternatively, the diameter of the flexible segment 120 may be same as for the remainder of the guidewire 100. Alternatively or in combination, the flexibility of the flexible segment 120 may be provided by having the flexible segment 120 being made of a different, more flexible material than the remainder of the guidewire 100, mechanically modifying the flexible segment 120 such as with slots or cuts, and/or modifying the flexible segment 120 with coating(s) in selected region(s) to increase stiffness in those region(s). For example, the flexible segment 120 may be cut into the shape of a coil spring.

As shown in FIG. 1, the atraumatic distal tip 110 may be rounded and have a greater diameter than the middle, flexible wire shaft portion 124 and the atraumatic distal tip 110 tapers down to the lesser diameter over the distal tapering portion 122. Alternatively, the micropuncture guidewire 100 may omit the distal tapering portion 122 such that the atraumatic distal tip 110 has a rounded end and the same diameter as the middle, flexible wire shaft portion.

The micropuncture guidewire 100 may further comprise an elongate wire shaft segment 130 proximal of the flexible segment 120. As shown in FIG. 1, the elongate segment 130 may have a diameter of 0.018". Alternatively, the elongate segment 130 may have the diameter of a standard guidewire, such as 0.035". The elongate segment 130 may be stiffer than the flexible segment 120. Rather than having a sharp transition from the greater diameter atraumatic distal tip 110 and the greater diameter elongate segment 130, the distal tapering portion 122 and the proximal tapering portion 126 gradually transition to the middle, flexible wire shaft portion 124. The distal tapering portion 122, the middle, flexible wire shaft portion 124, and the proximal tapering portion 126 may combine to significantly reduce friction of the entire micropuncture guidewire 100 and provide better feedback, thereby reducing the risks of inadvertent perforation and dissection. The middle, flexible wire shaft portion 124 may have substantially the same diameter throughout. The combined length of the distal tapering portion 122, the middle, flexible wire shaft portion 124, and the proximal tapering portion 126 may be 2-4 cm, for example.

Figure 2:
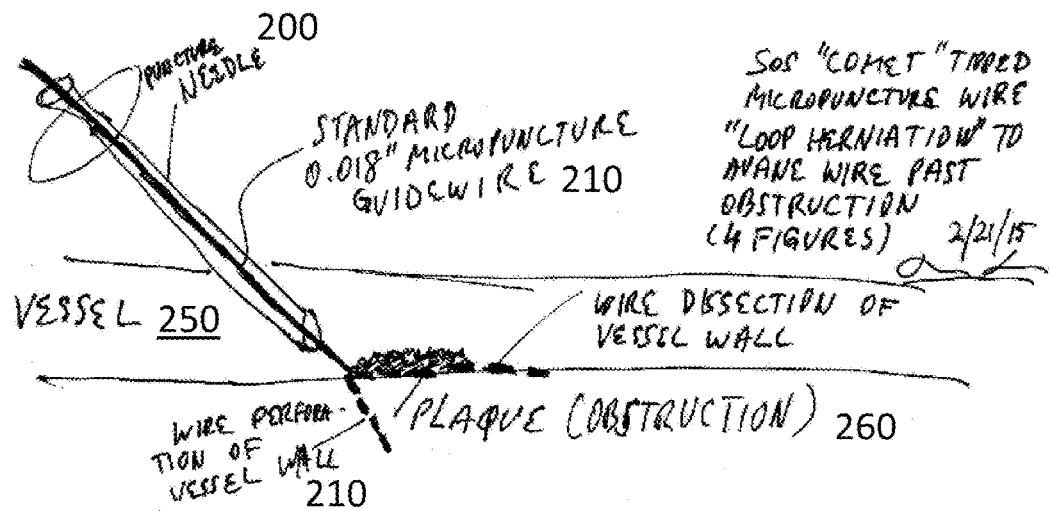
FIG. 2 shows a side, section view of a current, standard type micropuncture guidewire advanced into a blood vessel through an introducer needle.

FIG. 2 shows a side, section view of a current micropuncture guidewire 210 advanced into a blood vessel 250 through an introducer needle 200. As the guidewire 210 is advanced through the blood vessel 250, the guidewire 210 may encounter obstructions in the blood vessel 250 such as plaque 260. To move the guidewire 210 past the plaque 260, the operator may push the guidewire 210 with greater force. While attempting to advance the guidewire 210 past the plaque 260, the guidewire 210 may instead perforate or otherwise damage the wall of the blood vessel 250 in at least some cases. For instance, the guidewire 210 may encounter resistance from the inner lumen of the needle 200 and the operator may mistake the resistance from the plaque 260 as resistance from the needle 200. Due to the poor tactile feedback, the operator may inadvertently apply too much force to the guidewire 210 and perforate or otherwise damage the wall of the blood vessel 250.

Figure 3A:
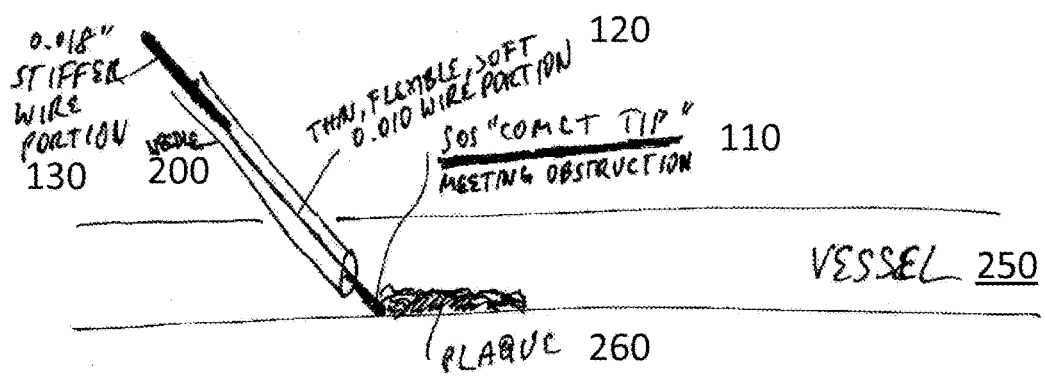
FIG. 3A shows a side, section view of the micropuncture guidewire of FIG. 1 advanced into a blood vessel through an introducer needle, according to many embodiments.
Figure 3B:
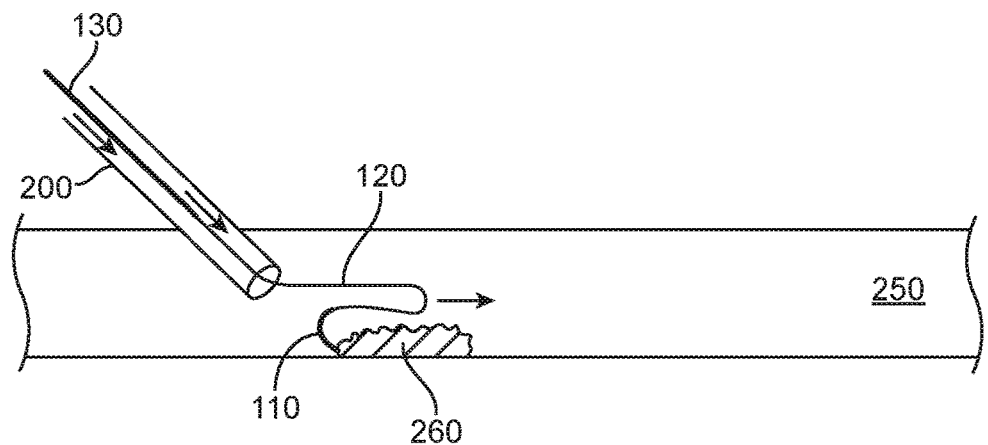
FIG. 3B shows a side, section view of the micropuncture guidewire of FIG. 1 and its flexible, neck segment forming into a loop as its distal tip encounters an obstruction in the blood vessel, according to many embodiments.
Figure 3C:
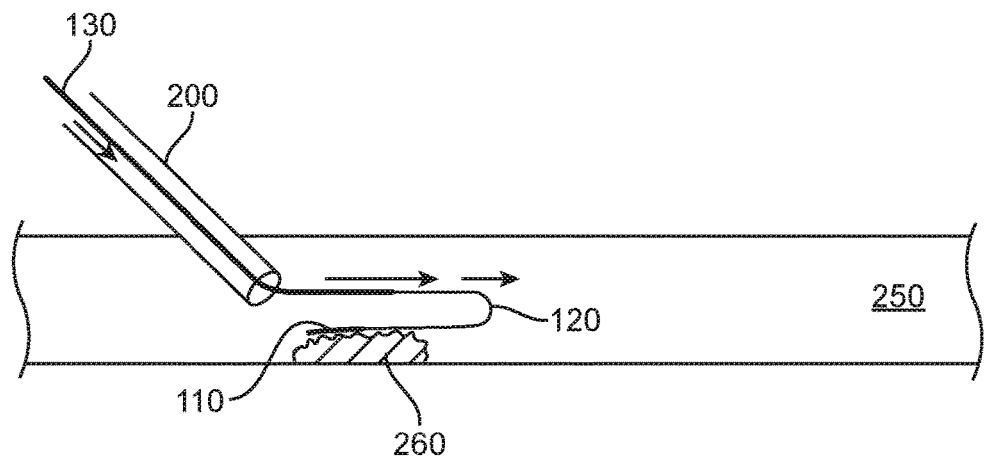
FIG. 3C shows a side, section view of the micropuncture guidewire of FIG. 1 and its flexible, neck segment advanced past the obstruction as a loop, pulling the distal tip distally past the obstruction, according to many embodiments.

FIG. 3A shows a side, section view of the micropuncture guidewire 100 advanced into the blood vessel 250 through the introducer needle 200. The atraumatic distal tip 110 and the tapered segment 122 may be advanced to encounter the plaque 260. In some embodiments, the smaller diameter of the flexible segment 120 may reduce the degree of friction encountered by the guidewire 100 as it is advanced through the introducer needle 200. In FIG. 3B, the guidewire 100 is further advanced into the blood vessel 250 such that the plaque 260 stops the advancement of the atraumatic distal tip 110 and the tapered segment 122 and the flexible segment 120 forms a loop distal of the atraumatic distal tip 110. In FIG. 3C, the guidewire 100 is even further advanced so that the stiffer elongate segment 130 pushes the looped flexible segment 120 beyond the plaque 260, pulling the distal tip 110 past the plaque 260 as well. Once the distal tip 110 and the flexible segment 120 are advanced past the plaque 260, the distal tip 110 and the flexible segment 120 may resiliently straighten such that the distal tip 110 is distal of the flexible segment 120 once more.

Figure 4A:
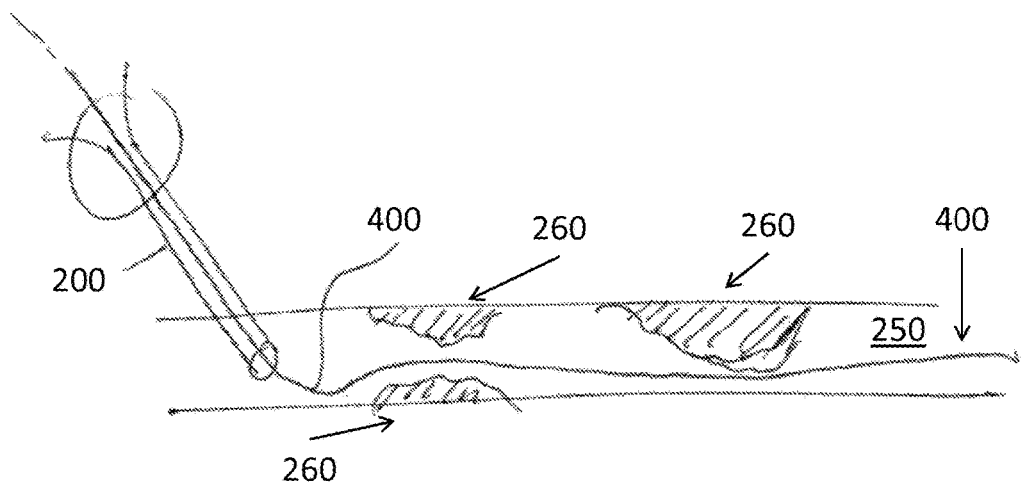
FIG. 4A shows a side section view of a current, standard type micropuncture guidewire being introduced into a blood vessel through an introducer needle.

FIGS. 4A to 4E show the standard method of advancing a micropuncture guidewire (e.g., 0.018" in diameter) and replacing it with a standard guidewire (e.g., 0.035" in diameter). FIG. 4A shows a standard micropuncture guidewire 400 being introduced into the blood vessel 250 through an introducer needle 200 penetrating tissue to access the blood vessel 250. The standard micropuncture guidewire 400 may have a diameter of 0.018" or the like throughout and one or more soldered segments at its tip and distal portion. In some embodiments, the atraumatic micropuncture guidewire 100 may be used in lieu of the standard micropuncture guidewire 400. The standard micropuncture guidewire 400 may be advanced further into the blood vessel to cross areas of extensive vascular disease such as plaques 260.

Figure 4B:
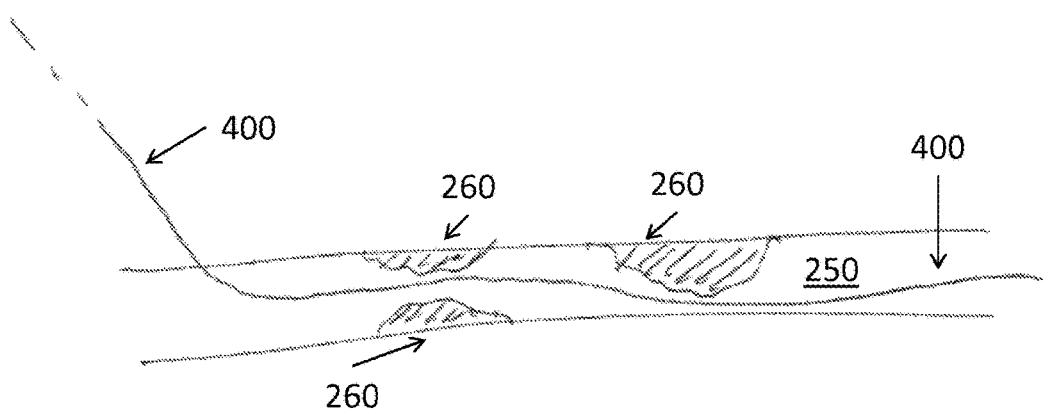
FIG. 4B shows a side section view of the micropuncture guidewire of FIG. 4A introduced into the blood vessel and the introducer needle withdrawn.

FIG. 4B shows the standard micropuncture guidewire 400 introduced into the blood vessel 250 and the introducer needle 200 withdrawn. In some embodiments, the introducer needle 200 may be retracted over the standard micropuncture guidewire 400 before the standard micropuncture guidewire 400 is further advanced. The introducer needle 200 may have inner lumen with a diameter closely matching the outer diameter of the standard micropuncture guidewire 400 and it may have soldered joints at or near its tip such that friction between the introducer needle 200 and the standard micropuncture guidewire 400 may impede the advancement of the standard micropuncture guidewire 400.

Figure 4C:
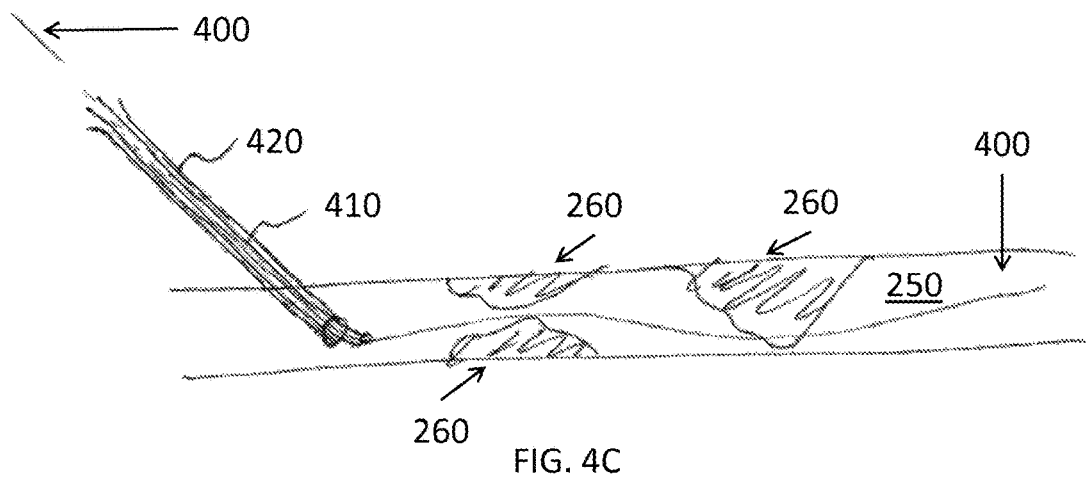
FIG. 4C shows a side section view of coaxial introducer dilators being introduced into the blood vessel over the micropuncture guidewire of FIG. 4A.

FIG. 4C an inner introducer sheath 410 and a coaxial outer introducer sheath 420 introduced into the blood vessel 250 over the standard micropuncture guidewire 400. The inner introducer sheath 410 may have an inner lumen with a diameter closely matching the outer diameter of the standard micropuncture guidewire 400. The inner introducer sheath 410 may be advanced over the standard micropuncture guidewire 400 outside the body before being advanced through the tissue tract over the standard micropuncture guidewire 400. The outer introducer sheath 420 may have an inner lumen with a diameter closely matching the outer diameter of the inner introducer sheath 410 and may be advanced thereover. The end of the outer introducer sheath 420 may be tapered to the outer diameter of the inner introducer sheath 410 to facilitate its advancement into the tissue tract as the inner introducer sheath 410 is advanced into the tissue.

Figure 4D:
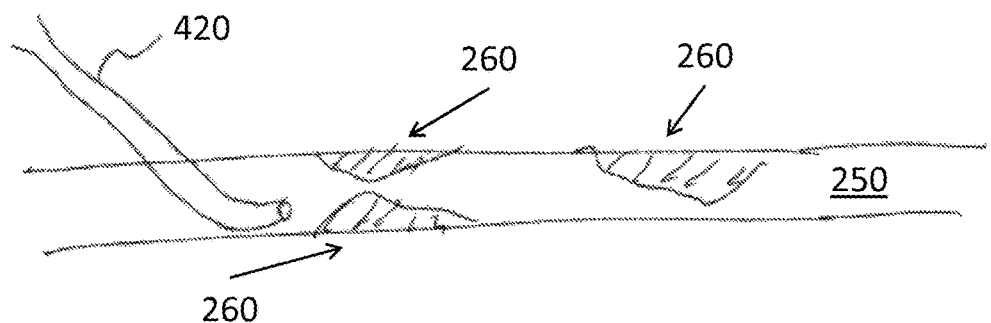
FIG. 4D shows a side section view of the micropuncture guidewire of FIG. 4A and the inner introducer dilator being withdrawn while the outer introducer dilator remains.
Figure 4E:
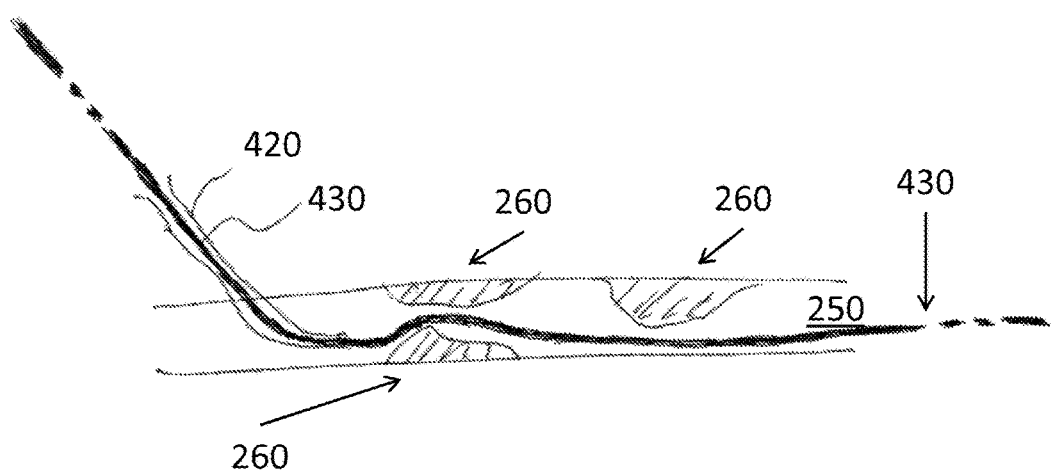
FIG. 4E shows a side section view of a standard 0.035" diameter guidewire being introduced into the blood vessel through the outer introducer dilator of FIG. 4C.

FIG. 4D shows the outer introducer sheath 420 remaining in the tissue tract to access the blood vessel 250. After the coaxial introducer sheaths 410, 420 are introduced into the blood vessel 250, the standard micropuncture guidewire 400 and the inner introducer sheath 420 may be withdrawn and removed so that a standard guidewire 430 may be advanced into the blood vessel 250, replacing the standard micropuncture guidewire 400 as shown in FIG. 4E. The standard guidewire 430 may have an outer diameter less than or equal to the diameter of the inner lumen of the outer introducer sheath 420. For example, the standard guidewire 430 may have a diameter of 0.035". As shown in FIG. 4E, the standard guidewire can be advanced further into the blood vessel 250.

The withdrawal of the standard micropuncture guidewire 400 and the later advancement of the standard guidewire 430 can be disadvantageous in at least some cases. There may be a greater likelihood of injury with the increased number of steps of withdrawal and advancement. The larger standard guidewire 430 may encounter difficulty or even failure in crossing one or more diseased vascular segments that the smaller micropuncture guidewire 400 had already successfully crossed through.

Aspects of the present disclosure also provide methods, systems, and devices for advancing larger diameter guidewires where a micropuncture guidewire has already been introduced to address at least some of the aforementioned disadvantages.

Figure 5A:
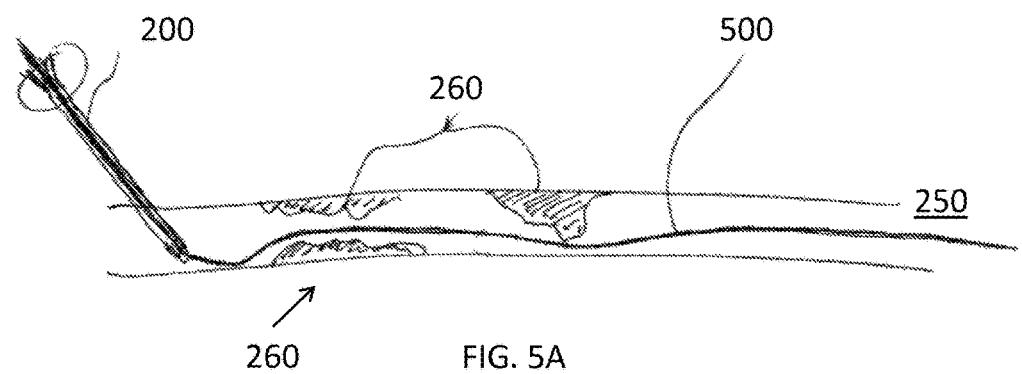
FIG. 5A shows a side section view of the micropuncture guidewire of FIG. 1 being introduced into a blood vessel through an introducer needle, according to many embodiments.

FIG. 5A shows a micropuncture guidewire 500 of the present disclosure being introduced into the blood vessel 250 through the introducer needle 200. The micropuncture guidewire 500 may have a uniform diameter throughout or may have an atraumatic distal tip as described above and herein. For example, the micropuncture guidewire 500 may have a diameter of about 0.018". As shown in FIG. 5A, the micropuncture guidewire 500 may be advanced through areas of the blood vessel which may include diseased regions such as plaque 260. After the micropuncture guidewire 500 is advanced, the introducer needle 200 may be withdrawn.

Figure 5B:
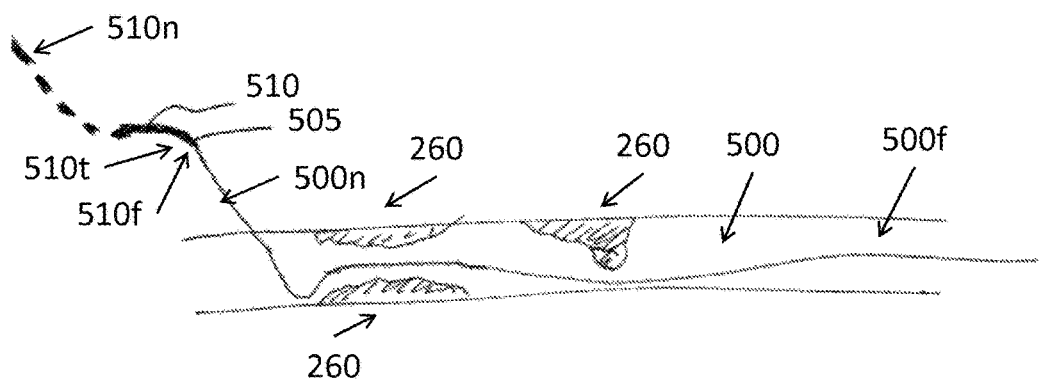
FIG. 5B shows a side section view of the micropuncture guidewire of FIG. 1 being coupled to a guidewire extension after the introducer needle has been withdrawn, according to many embodiments.

FIG. 5B shows the micropuncture guidewire 500 being coupled to a guidewire extension 510 with the introducer needle 200 having been withdrawn. The far end 500f of the micropuncture guidewire 500 has been advanced past the plaque 260. The near end 500n of the micropuncture guidewire 500 may couple to the far end portion 510f of the guidewire extension 510. The coupling 505 may occur outside of the subject. The diameters of the near end 500n and the far end portion 510f may be the same, such as 0.018". The guidewire extension 510 may comprise a far end portion 510f, a tapering transition portion 510t, and a near end portion 510n which may have the diameter of a standard guidewire or 0.035". The micropuncture guidewire 500 and the guidewire extension 510 may be constructed of the same materials or different materials. Examples of the materials include but are not limited to steel, stainless steel, copper, gold, silver, NiTi, to name a few. One or more of the micropuncture guidewire 500 and the guidewire extension 510 may be coated.

Figure 5C:
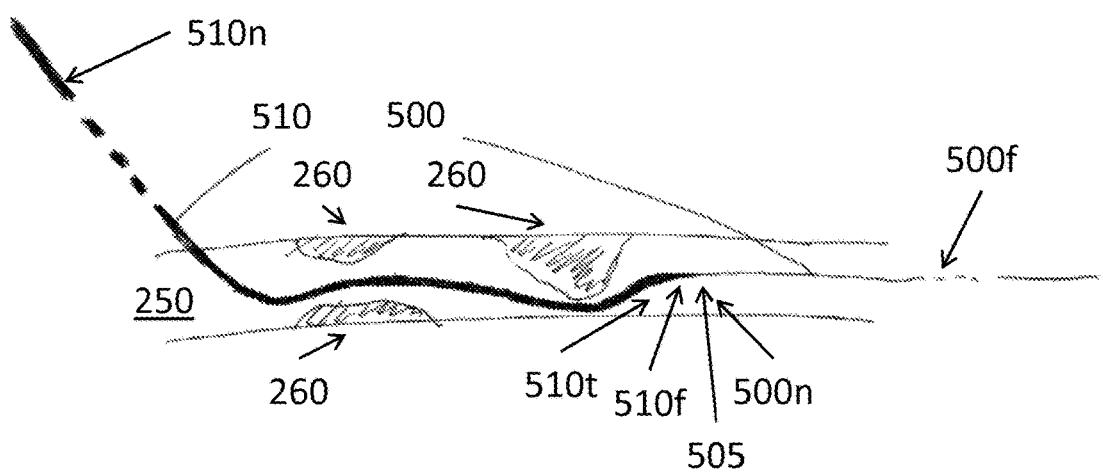
FIG. 5C shows a side section view the coupled micropuncture guidewire and guidewire extension of FIG. 5B being advanced further into the blood vessel; according to many embodiments.

FIG. 5C shows the coupled micropuncture guidewire 500 and guidewire extension 510 being advanced further into the blood vessel 250. The guidewire extension 510 may be advanced at least 10 cm into the blood vessel 250, for example. The transition portion 510t expands the tissue tract and blood vessel as it is advanced therethrough to minimize trauma to the tissue when the larger diameter guidewire extension 510 is advanced further into the blood vessel. An introducer sheath or other over-the-wire device which may require the outer diameter of the guidewire extension 510 can then be advanced over the guidewire extension 510 to access the blood vessel 250. The introducer sheath may be of various sizes such as 3, 4, or 5 Fr., for example. By coupling the micropuncture guidewire 500 and guidewire extension 510, a guidewire of a standard size (i.e., 0.035") can be introduced into blood vessel through an initial micropuncture (i.e., 0.018" in diameter) access without additional steps of withdrawing a smaller guidewire and re-advancing a larger guidewire using a succession of introducers 410 and 420 as shown in FIGS. 4A-4E.

Figure 5D:
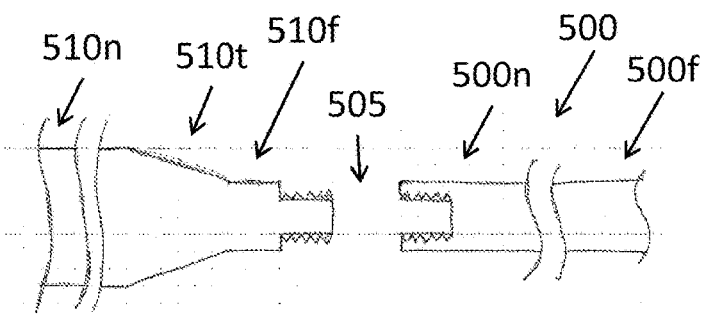
FIG. 5D shows a threaded fit between the micropuncture guidewire and the guidewire extension of FIG. 5B, according to many embodiments.
Figure 5E:
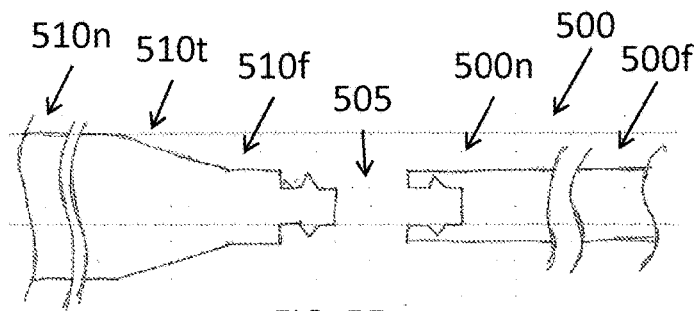
FIG. 5E show a snap fit between the micropuncture guidewire and the guidewire extension of FIG. 5B, according to many embodiments.
Figure 5H:
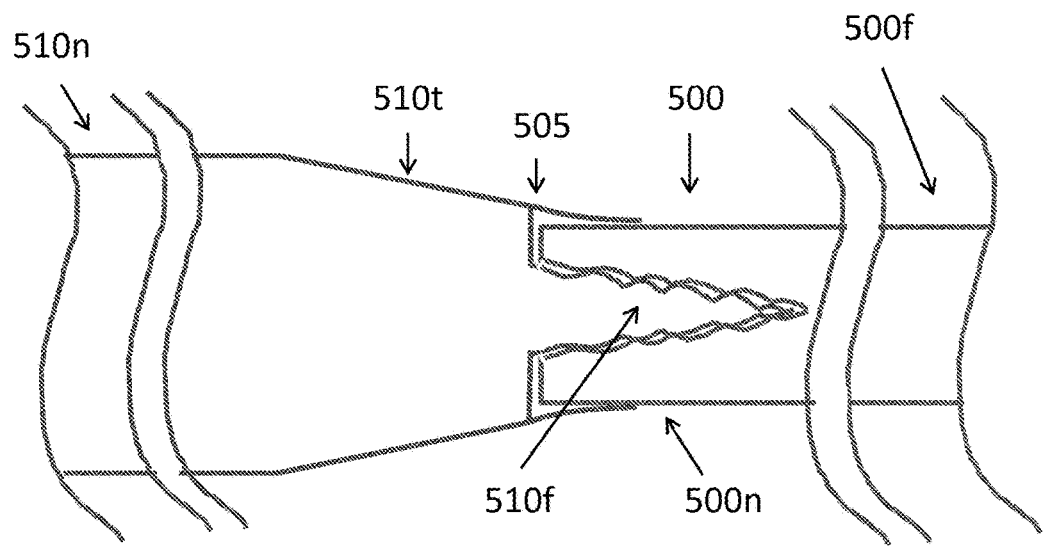
FIG. 5H shows another interference fit between the micropuncture guidewire and the guidewire extension of FIG. 5B, according to many embodiments.
Figure 5I:
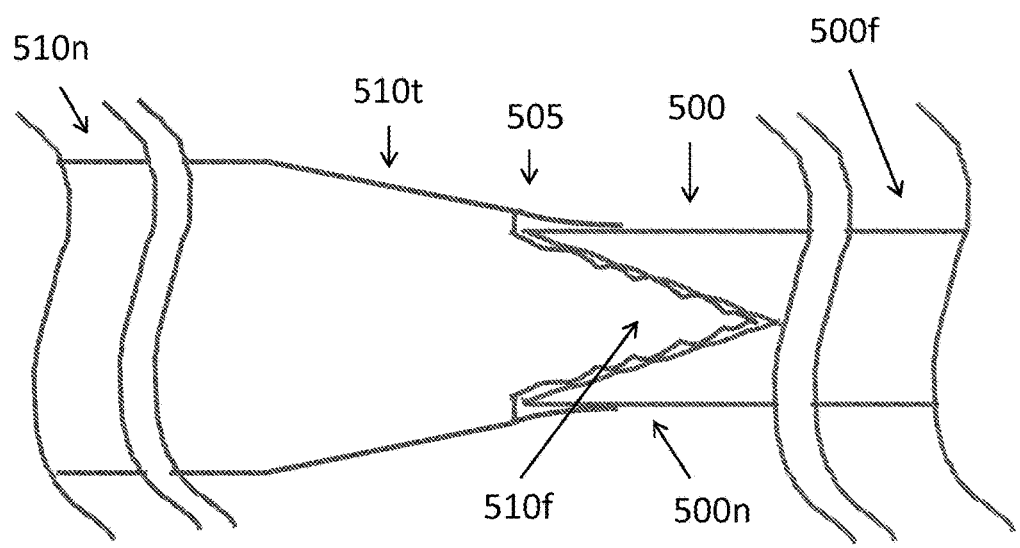
FIG. 5I shows another interference fit between the micropuncture guidewire and the guidewire extension of FIG. 5B, according to many embodiments.

The far end portion 510f of the guidewire extension 510 can be coupled to the near end 500n of the guidewire 500 in many ways. In an example shown by FIG. 5D, the coupling 505 may comprise a threaded fit between the threaded male connector of the far end portion 510 and the threaded female receptacle of the near end 500n. In another example shown by FIG. 5E, the coupling 505 may comprise a snap fit between the male connector of the far end portion 510 and the female receptacle of the near end 500n. In an example shown by FIG. 5F, the coupling 505 may comprise a snap fit of a different configuration between the male connector of the far end portion 510 and the female receptacle of the near end 500n. In an example shown by FIG. 5G, the coupling 505 may comprise an interference fit between the male connector of the far end portion 510 and the female receptacle of the near end 500. In some embodiments, the male and female parts are reversed.

Figure 5J:
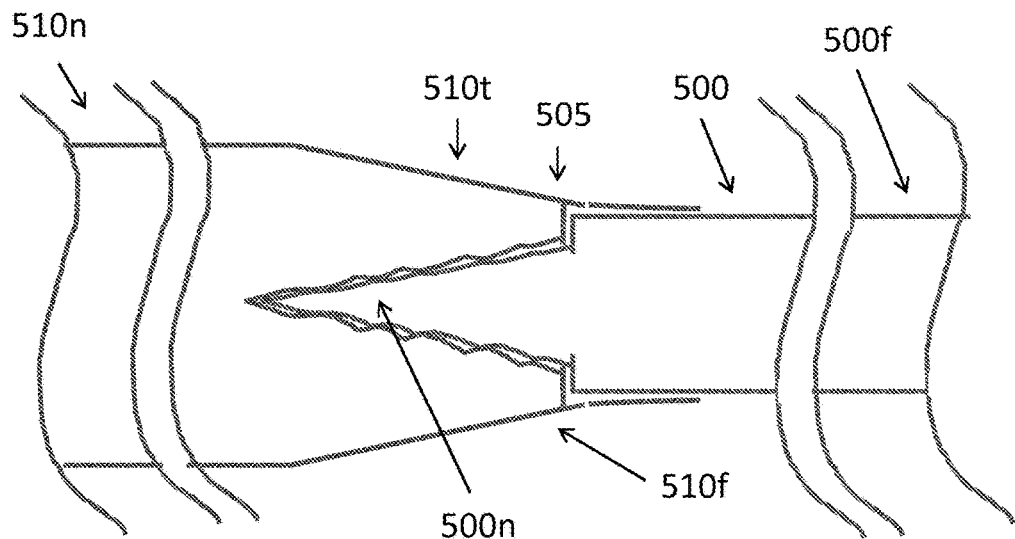
FIG. 5J shows another interference fit between the micropuncture guidewire and the guidewire extension of FIG. 5B, according to many embodiments.
Figure 5K:
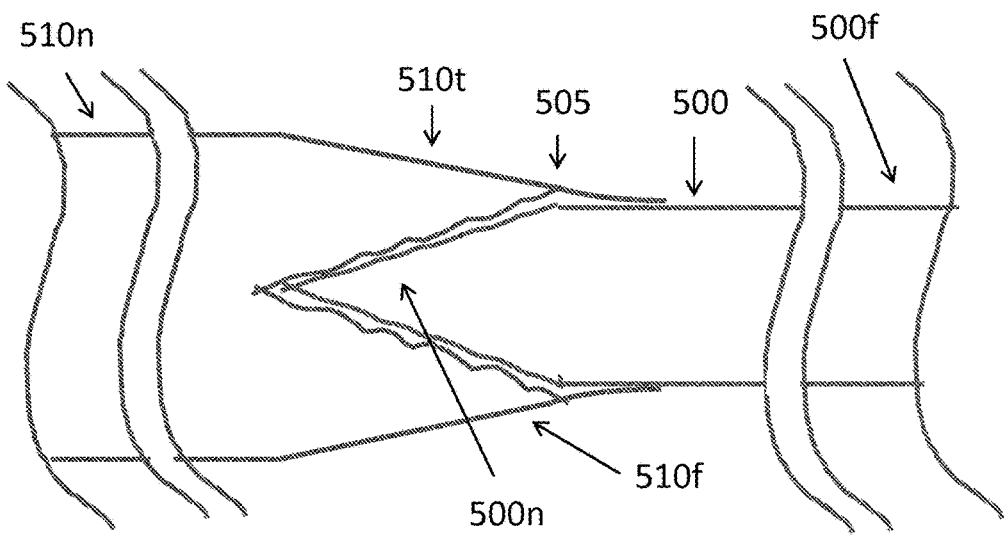
FIG. 5K shows another interference fit between the micropuncture guidewire and the guidewire extension of FIG. 5B, according to many embodiments.
Figure 5F:
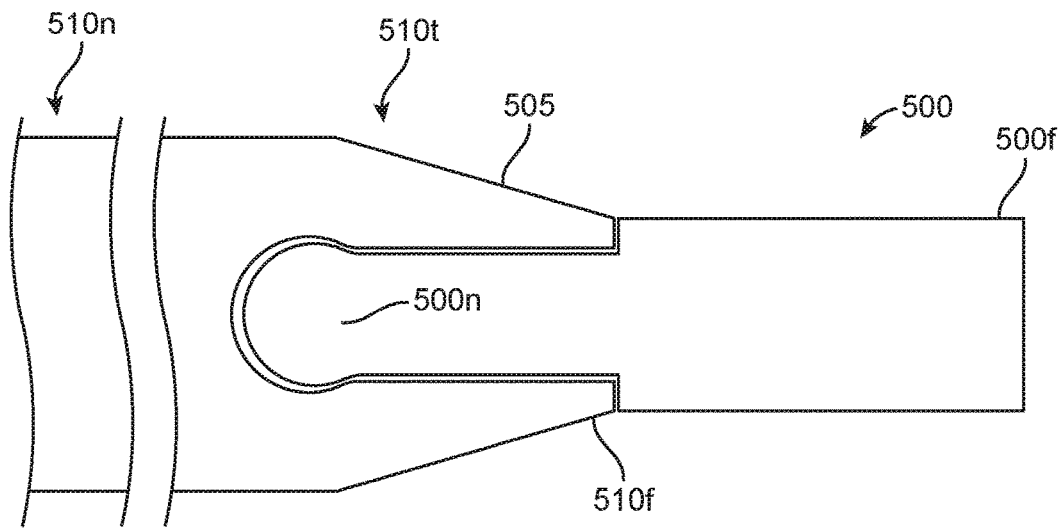
FIG. 5F shows another snap fit between the micropuncture guidewire and the guidewire extension of FIG. 5B, according to many embodiments.
Figure 5G:
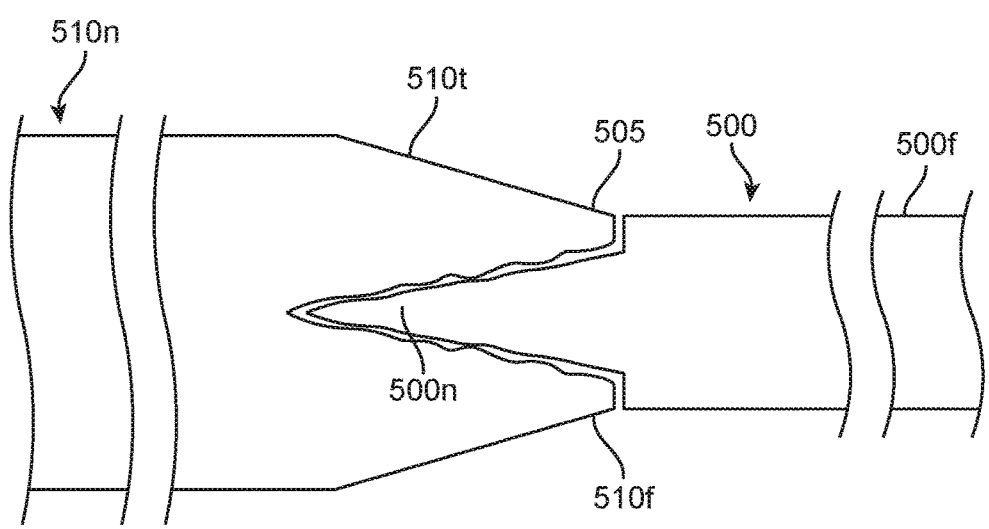
FIG. 5G shows an interference fit between the micropuncture guidewire and the guidewire extension of FIG. 5B, according to many embodiments.

Also provided herein are further embodiments of interference fits between the male connector of the far end portion 510f and the female receptacle of the near end portion 500n. In an example shown by FIG. 5H, the coupling 505 may comprise an interference fit between the far end portion 510f and the near end portion 500n in which the far end portion 510f of the male connector extends into the female receptacle of the near end 500. The far end portion 510f of the male connector may further comprise a tubular outer extension covering over the female receptacle of the near end 500 past the site of coupling 505. In another example shown by FIG. 5I, the coupling 505 may comprise an interference fit of a different configuration between far end portion 510f and near end portion 500n. The male distal end 510f of the far end portion 510 may extend into the female receptacle and may also comprise an outer extension covering over the female receptacle of the near end portion 500n with a gradually tapering far end 510f and a near end 500n with pointed ends. FIGS. 5J and 5K show examples where the male and female parts are reversed so that the far end portion 510 receives the near end tip 500n. In FIG. 5J, the coupling 505 may comprise an interference fit between the far end portion 510f and the near end portion 500n in which the ends of the far end portion 510f extend and cover the guidewire 500 past the site of coupling. In FIG. 5K, the coupling 505 may comprise an interference fit between the far end portion 510f and the near end portion 500n in which the ends of far end portion 510f extend and cover the guidewire 500 with a gradually tapering near end 500n and a far end 510f with pointed ends.

Figure 6:
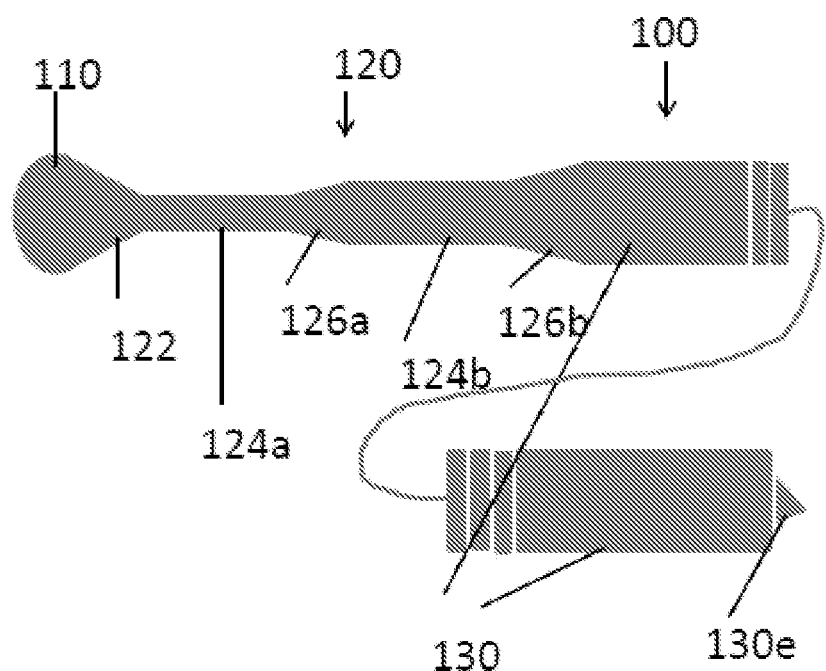
FIG. 6 shows a side view of a micropuncture guidewire with multiple tapered segments, according to many embodiments.

The micropuncture guidewire 100 may further have multiple segments of varying diameters between the atraumatic tip 110 and the stiff wire shaft 130. As shown in FIG. 6, the flexible segment 120 may comprise a distal tapering portion 122, a middle flexible wire shaft portion 124a, a proximal tapering portion 126a, a second flexible wire shaft portion 124b, and a second proximal tapering portion 126b. The diameter of the flexible wire shaft 124a may be 0.002-0.004" and the diameter of the wire shaft 124b may be 0.004." Each section may be narrower in diameter than the atraumatic tip 110 and the stiff wire shaft 130. The atraumatic tip 110 of a guidewire with multiple segments may have a diameter of a micropuncture guidewire, such as 0.018". Alternatively, the atraumatic tip 110 of a guidewire with multiple segments may have the diameter of a standard guidewire, such as 0.035". The stiff wire shaft 130 of a guidewire with multiple segments may have a diameter equal to or slightly smaller than that of the atraumatic tip 110. The micropuncture guidewire 100 with multiple segments may have a straight, curved (shaped) or shapeable proximal end and tip.

The stiff wire shaft 130 of a guidewire with multiple segments may have an end 130e suitable for coupling with an extension guidewire. The diameters of the stiff wire shaft 130 and the extension guidewire may be the same. Alternatively, the diameter of the extension guidewire may be of a greater diameter than the stiff wire shaft 130 and comprise a tapering transition portion and an end portion which may have the diameter of a standard guidewire or 0.035".

The micropuncture guidewire with multiple segments may be a one piece construction from a single material or may be constructed from different materials. In some embodiments, the micropuncture guidewire with multiple segments may lack the hemispheric tip 110 and comprise a flexible wire shaft portion 124a, a tapering portion 126a, a second flexible wire shaft portion 124b, a second tapering portion 126b, and the stiff wire shaft 130 which may have a coupling site for an extension guidewire.

The atraumatic guidewires described herein can eliminate many problems associated with conventional micropuncture guidewires. Because of the friction resulting from a conventional micropuncture guidewire advancing through the lumen of an introducer needle, an operator may not be able to differentiate whether resistance is due to friction of the guidewire within the needle or due to the guidewire tip meeting an obstruction in the bodily lumen such as a plaque in a blood vessel or other obstruction to its path. The operator may use too much force, resulting in the inadvertent puncture or dissection of the bodily lumen such as a blood vessel wall. By having tapered guidewire segments 126a and 126b and by lacking joints or welds between different guidewire components or segments, there is decreased contact between the wire and lumen of the needle, resulting in decreased friction and increased operator tactile feedback. The softer hemispheric tip 110 and the soft and flexible tapered segments 122, 124a, 126a, 124b, and 126b, for example, can also reduce complications resulting from the force exerted by the guidewire tip causing perforations, dissections, or other injuries to the blood vessel or viscus.

Additionally, by having an end 130e suitable for coupling an extension guidewire of a larger diameter, the present disclosure reduces the risks and inconveniences from using two coaxial dilators to introduce a larger diameter guidewire. With currently available micropuncture sets, when a larger diameter guidewire is needed, a coaxial double introducer dilator set is used to introduce an inner 0.018" diameter dilator and an outer 0.035" inner diameter dilator over the micropuncture wire. When the inner dilator and micropuncture guidewire are removed, the 0.035" dilator remains to allow the introduction of a larger 0.035" guidewire, which must successfully re-cross the segment of the vessel or body cavity previously crossed by the 0.018" micropuncture guidewire. This attempted re-crossing may fail or may pose an injury threat. The introducer set and re-crossing can be rendered unnecessary by having an end 130e on the micropuncture guidewire 100 that may couple to an extension guidewire, resulting in a one-step self-dilation of the entry site. Another advantage of the micropuncture guidewire 100 with multiple segments is that the single piece design, without joints, welds, or wrapping coils, can reduce complexity and cost of manufacturing.

FIG. 7A shows a micropuncture guidewire 500 initially introduced into the blood vessel 250 through a micropuncture needle that has been withdrawn. The micropuncture guidewire 500 may have a diameter of 0.018" and may have a length of 180 cm or, alternatively, a length greater than 180 cm. The micropuncture guidewire 500 may be substantially advanced through the micropuncture needle so that a short length, such as 20 cm, remains outside of the body.

As shown in FIG. 7B, an outer introducer sheath 700, with an inner dilator 710, may be advanced over the micropuncture guidewire 500. The outer introducer sheath 700 may have an inner diameter of various sizes such as 3, 4, or 5 Fr, or may be of a size greater than 5 Fr. The inner dilator 710 may have an outer diameter of various sizes such as 3, 4, or 5 Fr, or may be of a size greater than 5 Fr. The inner dilator 710 may have a tip 710t that is tapered, for example, to 0.018". The outer introducer sheath 700 and inner dilator 710 may have a length that is long enough to reach a site of pathology. Alternatively, the outer introducer sheath 700 and inner dilator 710 may have a short length, such as 10 cm, to remain in the iliac artery. The outer introducer sheath 700 may have a sidearm 720 with a stopcock.

Figure 7C:
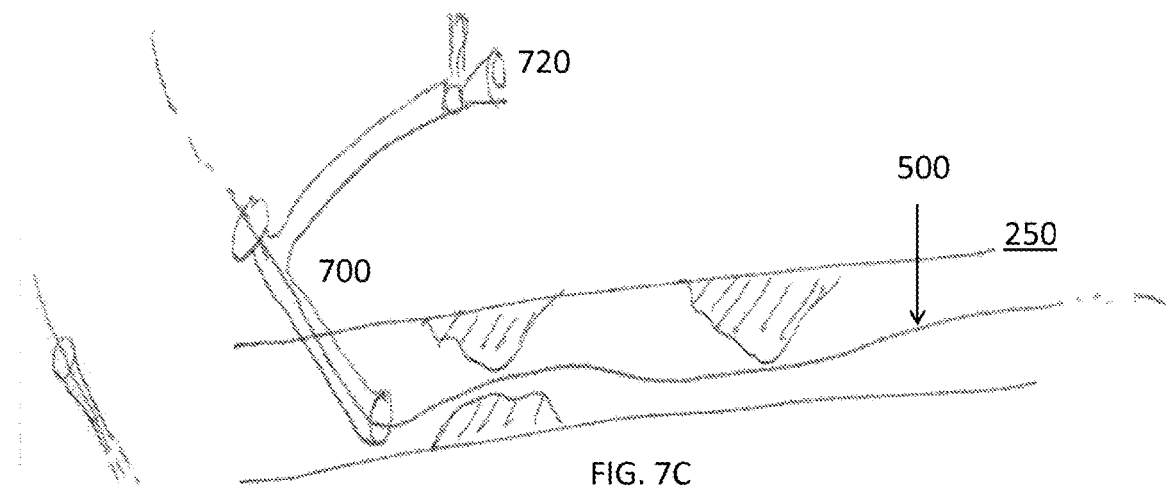
FIG. 7C shows a side section view of the micropuncture guidewire of FIG. 1 and the inner dilator being withdrawn while the outer introducer sheath remains.
Figure 7D:
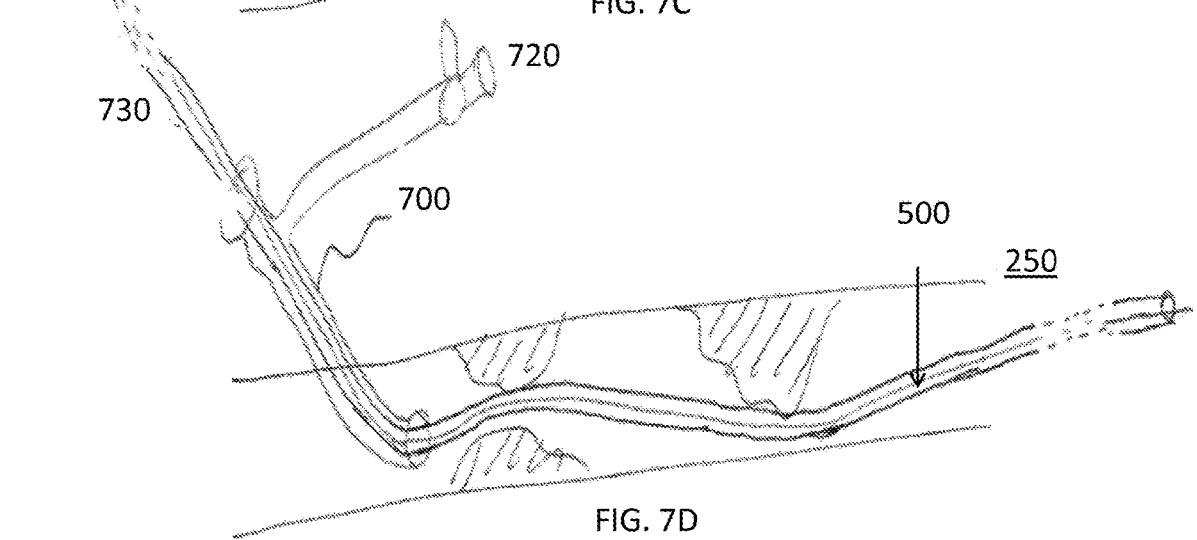
FIG. 7D shows a side section view of a catheter or other over-the-wire device being introduced into the blood vessel through the outer introducer sheath and over the micropuncture guidewire of FIG. 1.

FIG. 7C shows the outer introducer sheath 700 remaining in the blood vessel 250 after the inner dilator 710 has been removed. In FIG. 7D, a catheter or other over-the-wire device 730 may be introduced over the micropuncture guidewire 500 through the outer introducer sheath 700 and advanced into the blood vessel 250. The catheter or other over-the-wire device 730 may have an outer diameter less than or equal to the diameter of the inner lumen of the outer introducer sheath 700. The catheter or other over-the wire device 730 may have an inner diameter equal to or greater than 0.018". After introduction of the catheter or other over-the-wire device 730 into the blood vessel 250, the micropuncture guidewire 500 may be withdrawn and removed so that other guidewires may be advanced into the blood vessel 250, such as guidewires with an outer diameter equal to the inner diameter of the catheter or other over-the-wire device 730.

Figure 9:
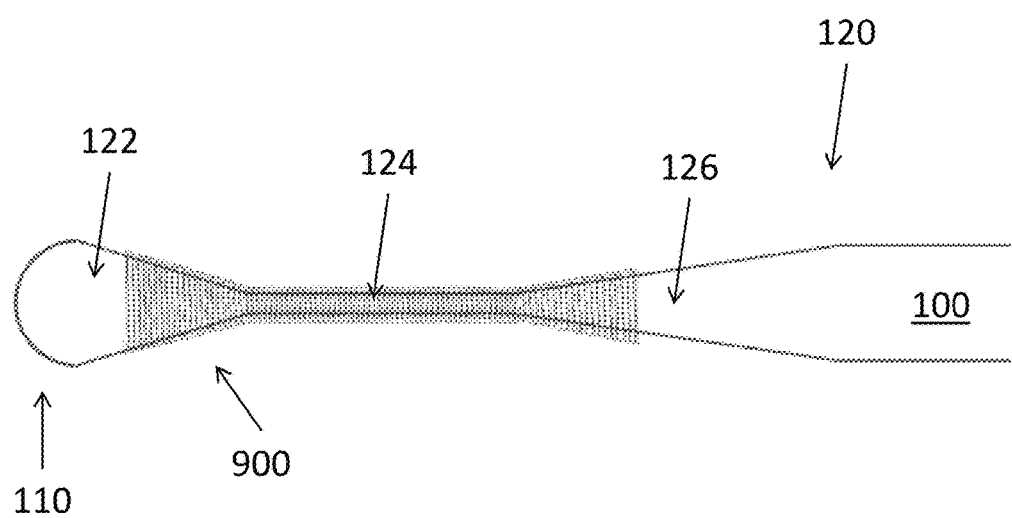
FIG. 9 shows a wire coil advanced over and supporting the flexible neck portion of a guidewire apparatus, according to many embodiments.

Further features may be provided to support the flexible neck segment of the guidewire apparatuses described herein, for example, as the guidewire apparatus is withdrawn into an introducer sheath or puncture needle. For example, a wire coil or braid may extend from the beginning of the "comet" taper 122 to the end of the second transition or taper 126 (referring to FIG. 1). Referring to FIG. 9, the support feature may comprise a wire coil 900 wound on the wire shaft (e.g., wire shaft 124) and can be attached on one or more of its proximal or distal ends to the (e.g., distal taper 122 and/or proximal taper 126) such as with glue, solder, or the like. Alternatively or in combination, the wire coil may be made of a material with shape memory characteristics (such as Nitinol) and can be configured to be shaped as a straight wire at very low temperatures but resumes a coil configuration after being applied to the wire shaft (e.g., wire shaft 124) at normal operating temperatures (e.g., body temperature). Alternatively or in combination, the support feature may comprise a wire coil or braid 800 (referring to FIGS. 8A-8D), which may be similar to many braided stent configurations. When pushed from its ends to shorten, the wire braid may increase in diameter so it can be slipped over the tip of the guidewire apparatus (e.g., tip 110) and subsequently pulled to its full length before attachment to the guidewire apparatus (e.g., at distal taper 122 and/or proximal taper 126) such as by glue, solder, or the like. Alternatively or in combination, the wire shaft may simply be cut or shaped to provide improved support when withdrawn. Such support features are further discussed as follows.

The thin tip segment between the proximal end of the comet tip (i.e., hemisphere 110 and decreasing taper 122) of the guidewire apparatus 100 and the expanding taper 126 to the full shaft diameter proximally is the often most vulnerable to being sheared off or being deformed during invasive procedures especially during introduction and withdrawal of the wire 100 through puncture needles or catheter based devices. Protecting or reinforcing this portion of the wire (i.e., the flexible segment 120) may be necessary. It may also be very important to retain the unique design characteristics of the guidewire tip: softness and flexibility, while reinforcing it. A thin wire braid 800 and/or a spiral coil 900 may add significant protection and reinforcement but very little extra stiffness and rigidity to the guidewire. The contours and narrower diameter of the thin segment 120 of the guidewire 100 over which the reinforcement is applied will typically not be augmented to the maximum diameter of the rest of the guidewire. Below are examples by which these design goals may be achieved:

Braid:

Referring to FIG. 8A, a wire braided "tube" 800 of suitable length and diameter is compressed to shorten it (e.g., along the axial/longitudinal directions indicated by arrows 801) and increase its diameter to be greater than that of the comet tip 110 or guidewire shaft flexible segment 120.

Referring to FIG. 8B, the compressed braid 800 can be slipped over the guidewire apparatus 100 such as indicated by the arrow 802.

Referring to FIG. 8C, the braid 800 can be stretched over the thinnest segment 120 of the guidewire apparatus 100 (e.g., along the axial/longitudinal directions indicated by arrows 803) and over the increasing diameter tapers 122, 126 at both its ends.

Referring to FIG. 8D, both ends of the braid 800 can be bonded to the increasing diameter tapers 122, 126 of the guidewire apparatus 100.

Spiral Coil:

There are at least three ways to apply a spiral wire coil 900 to the thinnest segment 120 of the guidewire apparatus 100 and to the expanding tapers 122, 126 at both its ends:

(A) Using Shape Memory Nitinol wire which changes shape at different temperatures:

The spiral wire coil 900 may comprise a shape memory metal (e.g., Nitinol) wire that may be shaped into a spiral coil configuration of suitable length and diameter and which can maintain that shape at body temperature. When chilled, the coil 900 can be manipulated and straightened for the assembly process.

The cold nitinol wire can then be suitably positioned with relation to the desired segment 120 of the guidewire apparatus 100.

The temperature of the coil 900 can be increased, allowing the coil 900 to remember it's shape. The coil 900 can be allowed to form into a spiral coil around the desired segment 120 of the guidewire apparatus 100.

Both ends of the spiral coil 900 are bonded to the increasing diameter tapers 122, 126 of the guidewire apparatus 100.

(B) Using a length of wire coil (similarly to the technique described above for the braid 800):

A wire coil "cylinder" 900 of suitable length and diameter can be formed with the turns maximally compressed.

The coil 900 can be slipped over the guidewire (as in FIGS. 8B and 8C, for example).

The coil 900 can be stretched and its two ends can be pulled over the thinnest segment 120 of the guidewire apparatus 100 and over the increasing diameter tapers 122, 126 at both its ends.

Both ends of the braid 900 can be bonded to the increasing diameter tapers 122, 126 of the guidewire apparatus 100.

(C) Using standard techniques of a winding spiral coil on a mandril:

Both ends of the guidewire apparatus 100 can be fixed and the coil 900 can be wound circumferentially over the desired portion of the guidewire apparatus 100 (e.g., the thin segment 120).

Both ends of the spiral coil 900 can be bonded to the increasing diameter tapers 122, 126 of the guidewire apparatus 100.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed in practicing the present disclosure. It is intended that the following claims define the scope of the invention and that methods and structures within the scope of these claims and their equivalents be covered thereby.

What is claimed is:

1. A guidewire apparatus advancable through a bodily lumen, the guidewire apparatus comprising:
    a hemispheric distal tip having an equator with a first diameter;
    a flexible neck segment proximal of the hemispheric distal tip and having a second diameter less than the first diameter of the hemispheric distal tip, the flexible neck segment having:
        (i) a middle portion having the second diameter,
        (ii) a distal tapering portion where the equator of the hemispheric distal tip tapers proximally to transition into the middle portion, and
        (iii) a proximal tapering portion proximal the middle portion;
    an elongate segment proximal of the proximal tapering portion of the flexible neck segment and having a third diameter greater than the second diameter of the flexible neck segment; and
    a wire-braided tube disposed over and supporting the flexible, neck segment,
    wherein the wire-braided tube comprises a distal tapering region and a proximal tapering region, the distal tapering region being configured to align with the distal tapering portion of the flexible neck segment, and the proximal tapering region being configured to align with the proximal tapering portion of the flexible neck segment,
    wherein the flexible neck segment is configured to form into a loop as the guidewire apparatus is advanced through the bodily lumen and the hemispheric distal tip encounters an obstruction, the loop being distal of the hemispheric distal tip within the bodily lumen, and
    wherein further advancement of the guidewire pushes the loop past the obstruction so that the hemispheric distal tip is pulled by the flexible neck segment past the obstruction.

2. The guidewire apparatus of claim 1, wherein one or more of the hemispheric distal tip, the flexible neck segment, or the elongate segment is covered with a coating.

3. The guidewire apparatus of claim 2, wherein the coating comprises a hydrophobic coating, a hydrophillic coating, an anti-thrombogenic coating, a polymeric coating, a silicone coating, or a polytetrafluoroethylene (PTFE) coating.

4. The guidewire apparatus of claim 1, wherein the guidewire apparatus is made of a material comprising one or more of platinum, gold, silver, NiTi, steel, steel alloy, stainless steel, stainless steel alloy, titanium, titanium alloy, aluminum, aluminum alloy, tungsten, or tungsten alloy.

5. The guidewire apparatus of claim 1, wherein the first diameter is about 0.018 inches.

6. The guidewire apparatus of claim 1, wherein the second diameter is about 0.010 inches.

7. The guidewire apparatus of claim 1, wherein the third diameter is about 0.018 inches.

8. The guidewire apparatus of claim 1, wherein the bodily lumen comprises a bodily duct, a bodily track, a bodily orifice, a bodily invagination, a blood vessel, an artery, a vein, a urethra, a ureter, a vagina, a fallopian tube, a rectum, a throat, an ear canal, a nasal tract, a bile duct, a biliary tract, an esophagus, a trachea, a bronchus, or an artificial bodily tract or lumen.

9. The guidewire apparatus of claim 1, wherein the obstruction comprises plaque in a blood vessel.

10. The guidewire apparatus of claim 1, wherein the hemispheric distal tip is biased to return to a position distal of the flexible neck segment within the bodily lumen after the loop of the flexible neck segment is advanced past the obstruction and the hemispheric distal tip is pulled past the obstruction.

11. The guidewire apparatus of claim 1, wherein the flexible neck segment is biased so that the loop straightens after the loop of the flexible neck segment is advanced past the obstruction and the hemispheric distal tip is pulled past the obstruction.

12. The guidewire apparatus of claim 1, wherein the wire-braided tube is removably attached to the flexible neck segment.

13. The guidewire apparatus of claim 1, wherein the wire-braided tube is disposed over and bonded to one or more of the distal tapering portion or the proximal tapering portion of the flexible neck segment.

14. The guidewire apparatus of claim 1, wherein a combined diameter of the wire-braided tube and the flexible neck segment is less than each of the first diameter of the hemispheric distal tip and the third diameter of the elongate segment.

15. The guidewire apparatus of claim 1, wherein the second diameter of the flexible, neck segment is less than the first diameter such that the flexible, neck segment is more flexible than the hemispheric distal tip.

16. The guidewire apparatus of claim 1, wherein the third diameter of the elongate segment proximal of the neck segment is greater than the second diameter of the flexible, neck segment such that the flexible, neck segment is more flexible than the elongate segment proximal thereto.

17. A guidewire apparatus advancable through a bodily lumen, the guidewire apparatus comprising:
   an atraumatic distal tip having a first diameter;
   a flexible segment proximal of the atraumatic distal tip and having a second diameter less than the first diameter, the flexible segment comprising a middle portion having the third diameter and tapering proximal and distal portions having diameters greater than the third diameter;
   an elongate segment proximal of the flexible segment and having a third diameter greater than the second diameter;
   a wire-braided tube disposed over and supporting the flexible segment,
   wherein the wire-braided tube comprises a middle region, a distal tapering region, and a proximal tapering region configured to align with and be disposed over the middle portion, the distal tapering portion, and the proximal tapering portion, respectively, of the flexible segment, the distal and proximal tapering regions of the wire-braided tube having diameters greater than a diameter of the middle region,
   wherein the flexible segment is configured to form into a loop as the guidewire apparatus is advanced through the bodily lumen and the atraumatic distal tip encounters an obstruction, the loop being distal of the atraumatic distal tip, and
   wherein further advancement of the guidewire pushes the loop past the obstruction so that the atraumatic distal tip is passed through the obstruction.

18. The guidewire apparatus of claim 17, wherein one or more of the atraumatic distal tip, the flexible segment, or the elongate segment is covered with a coating.

19. The guidewire apparatus of claim 17, wherein one or more of the atraumatic distal tip or the elongate segment comprises a first material, and wherein the flexible segment comprises a second material different from and more flexible than the first material.

20. The guidewire apparatus of claim 17, wherein one or more of the atraumatic distal tip or the elongate segment comprises a first material, wherein the flexible segment comprises further comprises the first material, and wherein the flexible segment is mechanically modified to be more flexible than one or more of the atraumatic distal tip or the elongate segment.

21. The guidewire apparatus of claim 20, wherein the flexible segment has one or more slots or cuts to provide flexibility.

22. The guidewire apparatus of claim 17, wherein the atraumatic distal tip is biased to return to a position distal of the flexible segment after the loop of the flexible segment is advanced past the obstruction and the atraumatic distal tip is pulled past the obstruction.

23. The guidewire apparatus of claim 17, wherein the flexible segment is biased so that the loop straightens after the loop of the flexible segment is advanced past the obstruction and the atraumatic tip is pulled past the obstruction.

24. The guidewire apparatus of claim 17, wherein the bodily lumen comprises a blood vessel and the obstruction comprises plaque in the blood vessel.

25. The guidewire apparatus of claim 17, wherein the wire-braided tube is removably attached to the flexible segment.

26. The guidewire apparatus of claim 17, wherein the wire-braided tube is disposed over and bonded to one or more of a distal transition region between the atraumatic distal tip and the flexible segment or a proximal transition the flexible segment.

27. The guidewire apparatus of claim 17, wherein a combined diameter of the wire-braided tube and the flexible segment is less than a diameter of the atraumatic distal tip and a diameter of the elongate segment.

* * * * *